United States Patent [19]

Krauter et al.

[11] Patent Number: 5,496,260
[45] Date of Patent: Mar. 5, 1996

[54] TORQUE OVERRIDE KNOB FOR ENDOSCOPES, BORESCOPES, OR GUIDE TUBES

[75] Inventors: Allan I. Krauter, Syracuse; Michael P. Kehoskie, Jordan; Robert L. Vivenzio, Auburn, all of N.Y.

[73] Assignee: Welch Allyn, Inc., Skaneateles Falls, N.Y.

[21] Appl. No.: 243,390

[22] Filed: May 16, 1994

[51] Int. Cl.⁶ ............................. A61B 1/00; A61B 1/005
[52] U.S. Cl. ............................................. 600/148; 600/146
[58] Field of Search .................................. 128/4; 403/41, 403/112, 113, 117, 350; 600/146, 147, 148

[56] References Cited

U.S. PATENT DOCUMENTS 5,007,406  4/1991  Takahashi et al. ........................... 128/4

Primary Examiner—Richard J. Apley
Assistant Examiner—Beverly M. Flanagan
Attorney, Agent, or Firm—Harris Beach & Wilcox

[57] ABSTRACT

A manually rotated knob drive mechanism incorporates a torque override feature. If the knob turning force exceeds a predetermined torque limit the feature permits slippage between the knob and the associated stem or drive shaft. The knob can continue to rotate, under slippage, until the knob and stem are aligned at a predetermined mutual orientation, or home position. This occurs at only one home position. The torque override feature is formed of an insert molded into the knob, and having a bore in which there is an annular shoulder. A hub member fits into the insert and has an annular surface that faces the insert shoulder. The hub member attaches to the stem or shaft and a spring yieldably urges the hub member against the insert. There are protuberances on the insert shoulder and corresponding grooves or recesses on the hub member annular surface, which coincide with one another only at the home position. The knob drive can be employed on the steering control handle of a borescope, endoscope or guide tube.

11 Claims, 3 Drawing Sheets

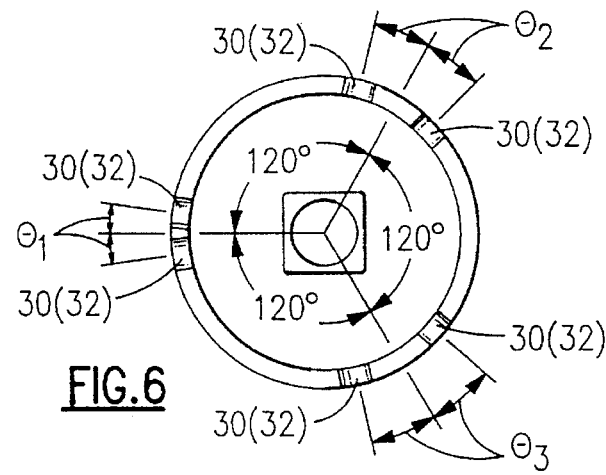
FIG. 6
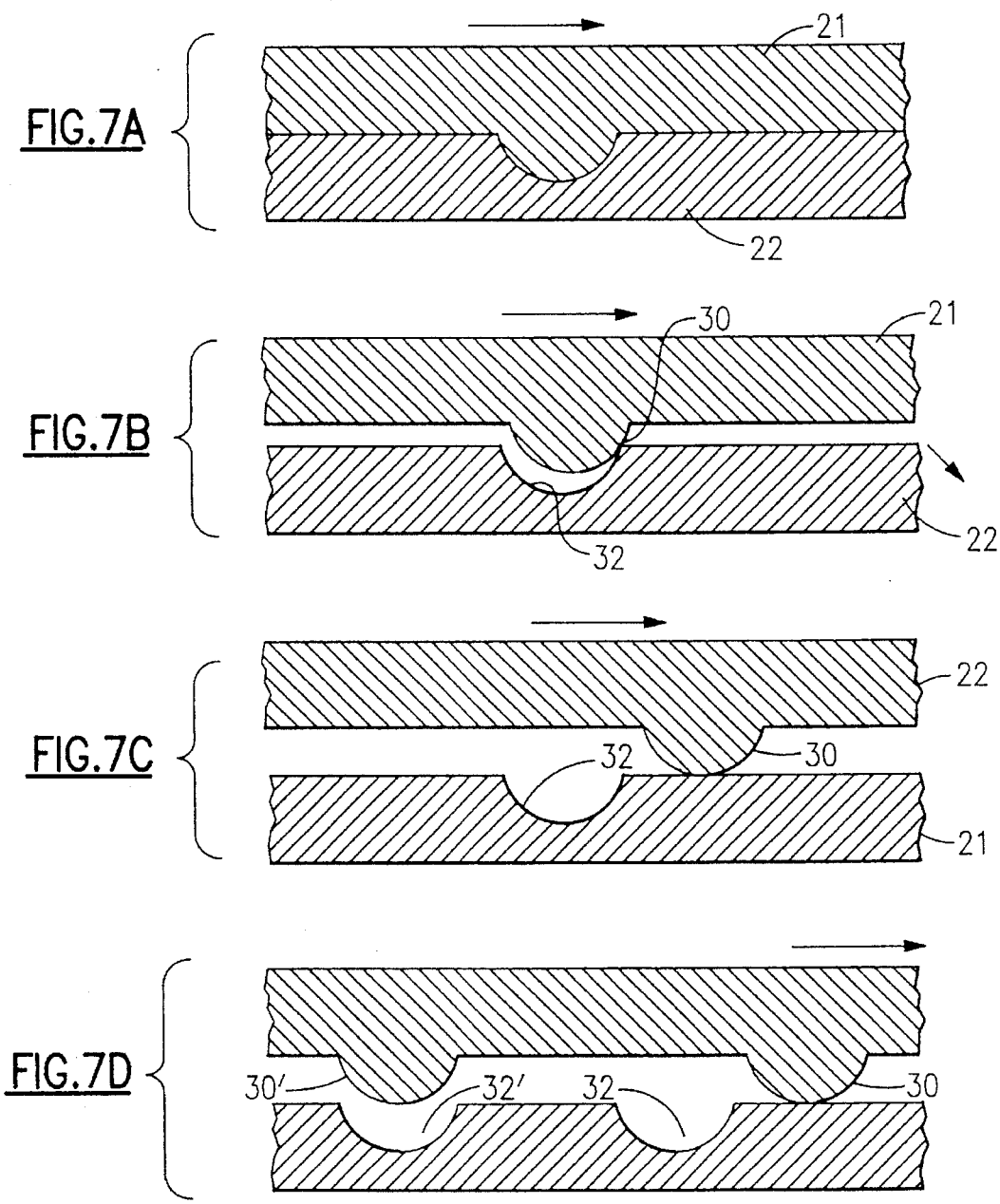
FIG. 7A
FIG. 7B
FIG. 7C
FIG. 7D

TORQUE OVERRIDE KNOB FOR ENDOSCOPES, BORESCOPES, OR GUIDE TUBES

BACKGROUND OF THE INVENTION

This invention relates to manually rotatable controls, and is particularly directed to a hand-rotated knob drive for rotating a shaft-driven device. The invention is more particularly concerned with a torque override mechanism in the knob drive that normally engages the knob and its associated drive stem, but effects disengagement if a predetermined maximum torque is exceeded.

The invention is favorably employed in the control handle of a cable actuated steerable probe such as an endoscope, borescope or guide tube, in which the steering knob is rotated clockwise or counter-clockwise to effect bending in one direction or the other in a bending plane.

With borescopes, endoscopes or guide tubes of this type, the users can apply excessive torque to the steering knob, or to both steering knobs in the case of a four-way steerable probe. If the bending neck of the probe is restricted against further articulation, tension in the associated steering cable can become high. This can cause damage such as cable stretch, or can pull off an associated cable terminator, or can damage the steering mechanism. If the steering is restricted because the probe's bending neck is lying against the wall of a body cavity, excess torque can result in tissue damage to the cavity wall or to an adjacent organ.

If the bending neck is not restricted, the steering mechanism encounters stops disposed on ends of toothed racks of the mechanism or elsewhere in the probe. If excessive torque is applied to the steering knobs after the stops are encountered, internal damage can result to the probe.

OBJECT AND SUMMARY OF THE INVENTION

Accordingly, it is an object of this invention to provide a steering knob mechanism which functions normally as long as the applied torque is within predetermined limits, but which will disengage the knob from the associated drive stem if a predetermined maximum torque is exceeded.

It is another object to permit the user to maintain steering orientation, such that after the predetermined maximum torque has been exceeded, the knob and stem will reengage only when rotationally aligned at a specific orientation.

It is a related object to provide a torque override mechanism which permits the steering knob orientation, relative to the angulation of the bending neck, to be easily recoverable without removing the instrument from its respective application.

It is a further object to provide a torque override steering knob mechanism that is interchangeable with a conventional steering knob, thereby facilitating retrofit.

It is a still further object to provide an improved steering knob which is reliable and predictable, and which operates in both directions of knob rotation.

It is yet another object to provide an improved steering knob that permits the torque setting to be easily changed.

According to an aspect of this invention, a hand-rotatable knob drive comprises a knob, a drive stem or shaft that actuates a rotary mechanism, and a torque override feature that couples the knob to the stem. The torque override feature serves to engage the knob and the stem, but permits rotational slippage when a predetermined torque is exceeded. The override feature reengages the stem and the knob only when the knob is rotated, under slippage, to the point at which the knob and stem are aligned at a predetermined mutual orientation. This occurs at a unique position, i.e., at one and only one mutual orientation.

In a preferred mode the torque override feature is formed by an insert that is molded into the knob and a hub portion that fits into the insert. The insert has an axial bore with an annular internal flange that forms an annular shoulder. The hub member fits inside the bore of the insert and has a recess that defines an annular shoulder. The shoulder of the hub member faces against the shoulder of the insert, and a disc spring or other resilient means yieldably urges the shoulders against each other. On one shoulder there are protuberances distributed around it. These can be pins or other cylindrical members oriented radially with a surface protruding above the surface of the respective shoulder. The other shoulder has corresponding grooves formed in it.

The positions of the protuberances (and of the grooves) are unequally spaced, so that the grooves and protuberances align only at one position.

When torque on the knob exceeds the predetermined torque limit, which depends on the geometry of the protuberances and grooves and on the spring constant and preload of the disc spring, the protuberances rise out of their respective grooves. If there is continued rotation of the knob, the protuberances ride upon the shoulder of the other member. If any one of the protuberances aligns with a groove, the rest of the protuberances are out of alignment with the other grooves, except at the unique position where all the grooves and all the protuberances are aligned.

In a preferred mode, the torque override characteristics are symmetrical, i.e., the same in both steering directions. However, for a given application, it is possible to engineer the device to require more torque in one direction than in the other.

The above and many other objects, features, and advantages of this invention will become apparent to those skilled in the art from the ensuing description of a preferred embodiment of the invention, which should be read in conjunction with the accompanying Drawings.

BRIEF DESCRIPTION OF THE DRAWINGS

FIG. 6 is a schematic plan view of the hub member showing angular orientation of the engaging grooves.

FIGS. 7A to 7D are schematic views for explaining the operation of this embodiment.

DETAILED DESCRIPTION OF THE PREFERRED EMBODIMENT

Figure 1:
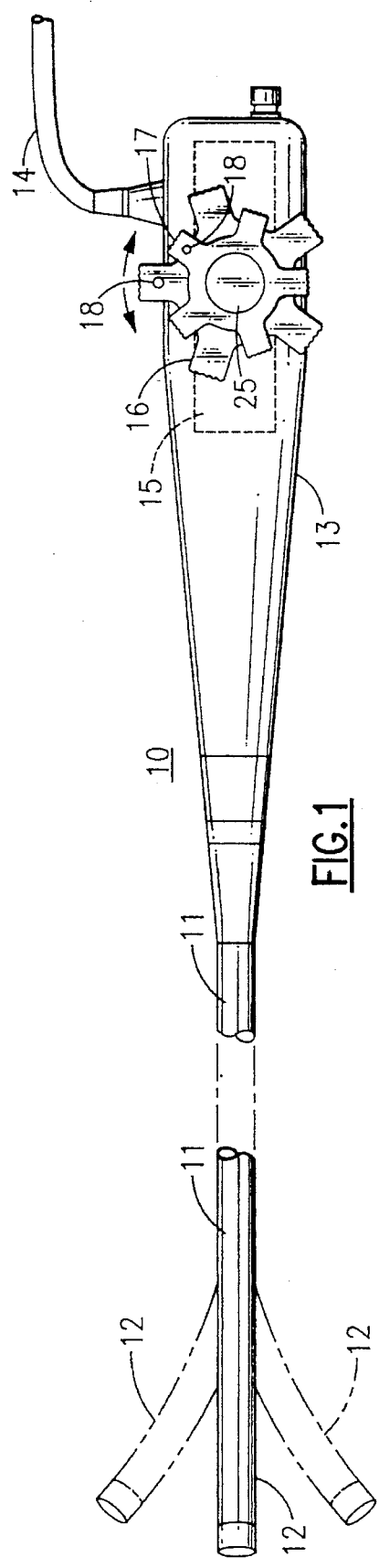
FIG. 1 is a partial perspective view of a steering control handle and a bending neck of a steerable probe which incorporates steering knobs according to an embodiment of this invention.

With reference to the Drawing, FIG. 1 shows a borescope or endoscope 10, which can be any flexible elongated steerable probe. This probe can be of the optical type (i.e., fiberscope) in which an optical image is carried on a coherent fiber optic bundle, or the video type, in which a miniature camera is disposed in the distal tip of the probe. Here, the borescope or endoscope 10 has a flexible elongated insertion tube 11 having a steerable bending neck 12 disposed at its distal tip. A proximal end of the insertion tube 11 enters a control handle 13, from which an umbilical 14 emanates. The latter carries image information back to a viewer or image processor (not shown) and carries illumination which is brought forward through the insertion tube 11 to illuminate objects in the viewing zone of the probe. Here, the control handle 13 contains a manually actuated steering mechanism 15 for effecting steering of the bending section 12 in the up/down sense and in the right/left sense. This mechanism 15 has an inner knob 16 to control up/down steering and an outer knob 17 to control right/left steering. Turning the knob 16 moves the steering section 12 to one or the other of the positions shown in ghost lines.

Each knob has an index 18, which can be a circular recess on one lobe of the respective knob 16, 17. This is intended to give the operator a visual and/or tactile confirmation of the bending orientation of the bending neck 12.

In this embodiment the knobs are molded of a hard rubber or rubber-like material, each with five radial lobes. The knobs 16,17 are disposed adjacent each other on a common axis. However, other possible arrangements exist, and would be within the ambit of this invention.

Figure 2:
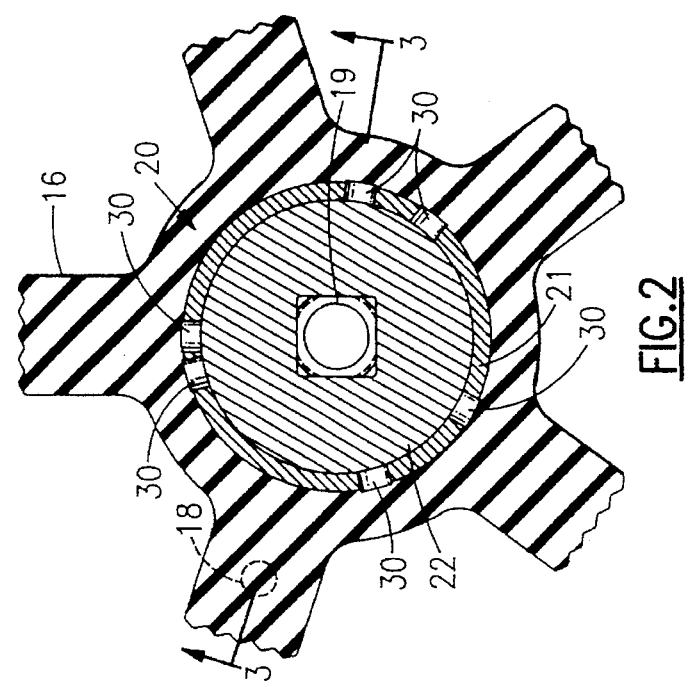
FIG. 2 is a cross sectional view of a torque override knob mechanism according to this embodiment.
Figure 5:
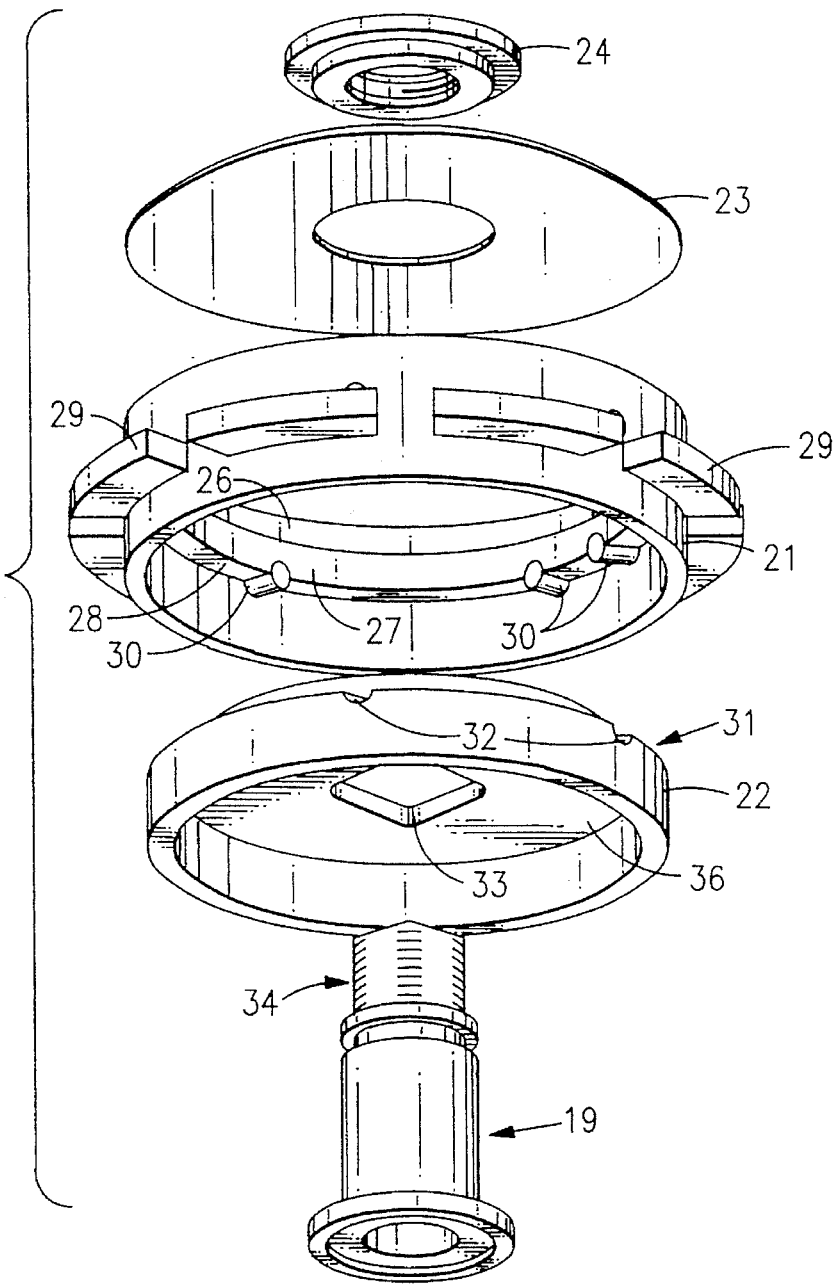
FIG. 5 is an exploded view of the knob and torque override mechanism of this embodiment.

The knob mechanism is shown in cross section in FIGS. 2 and B and in an exploded assembly form in FIG. 5. Here knob 16 is chosen as typical, but the mechanism in the other knob 17 would be substantially identical.

The knob assembly includes a torque override feature 20 which links the knob 16 to the stem or shaft 19, but permits slippage of the knob relative to the shaft if a predetermined torque limit is exceeded. This limit can be programmed so as to be less than a stress damage threshold for the associated bending neck 12, steering cables (not shown), or elements of the steering mechanism 15.

Figure 4:
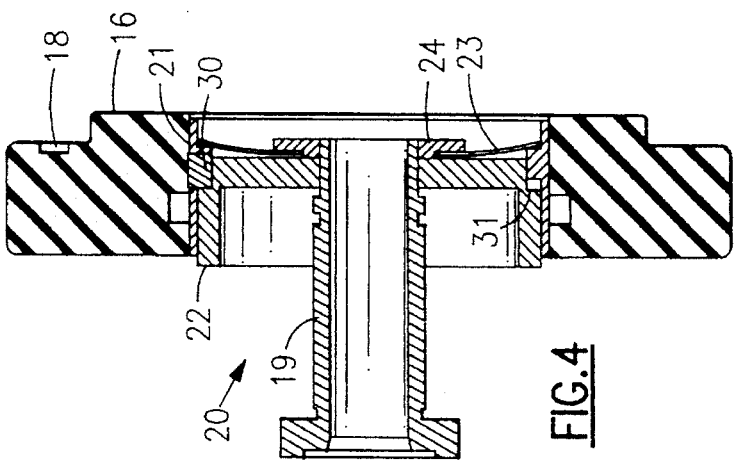
FIG. 4 is a section view. Similar to FIG. 2 showing displacement and spring flexion occurring on torque override.
Figure 3:
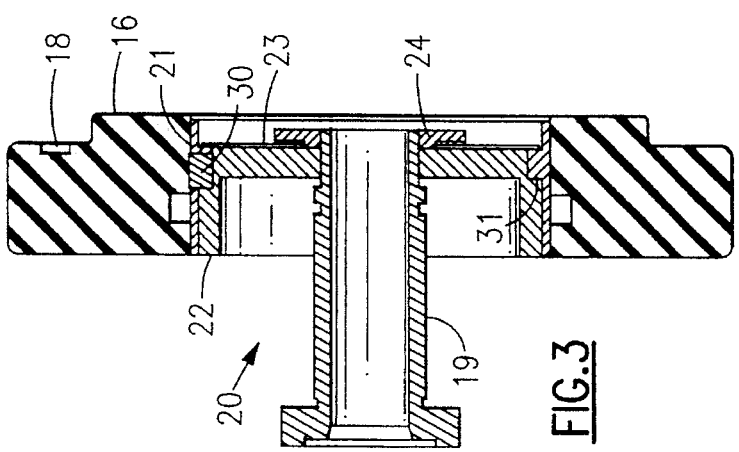
FIG. 3 is a sectional view taken at 3—3 of FIG. 2.

The torque override feature 20 is formed by a combination of a metal insert 21 that is molded in place in the knob 16 and a hub member 22 that is disposed coaxial with the insert 21. A flat spring 23 yieldably biases the hub member 22 against the insert 21, and a retaining nut 24 holds the combination of the insert 21, hub member 22 and spring 23 in place on the drive shaft or stem 19. When the torque override comes into play, there is axial deflection between the hub 22 and insert 21, and flexure of the spring 23, as illustrated in FIG. 4. The cross sectional view of the knob and insert is the same in FIG. 4 as in FIG. 3. The cross section of the hub member of FIG. 4 is between positions of the detents.

As better shown in FIG. 5, the knob insert 21 is generally cylindrical with a central axial bore 26. An annular flange 27 projects radially into the bore and defines an axial shoulder 28 having a flat surface. On the outside of the insert 21 are a number of radial fins or flanges 29, which lock to the hard rubber knob 16 when it is molded onto the insert.

In this embodiment, a plurality of pins 30 are situated with their axes directed radially on the insert 21, and with cylindrical surfaces projecting above the flat surface of the shoulder 28. Here there are six of these pins, arranged at uneven angular spacings about the shoulder 28, for reasons to be discussed shortly.

The hub member 22 is a cylindrically shaped metal member with a flat disc end 36, and with an annular recess at its outer rim defining a shoulder 31 on which are formed a plurality of grooves or recesses 32. In this embodiment, the grooves 32 are concave cylindrical grooves with axes oriented in the radial direction of the hub member 22. Here there are six of these grooves 32, arranged on the shoulder 31 so that they line up with the pins 30 of the insert 21, but do so only at one rotational position.

The hub member 22 has a square center opening 33 that fits a threaded square end 34 of the shaft 19. The spring disc 23 is positioned over the threaded shaft end 34, and is clamped in place with the retaining nut 24. The outer rim of the spring disc 23 rests on the side of the flange 27 opposite the shoulder 28 and pins 30. The rim of the retaining nut 24 has an undercut rim so as not to inhibit flexure of the spring 23 in the vicinity of the nut 24.

As shown in FIG. 6, in this embodiment the pins 30 as are the associated grooves or recesses 32, are positioned along the annular shoulder in a fashion such that two things occur:

a) The lifting of pins 30 out of grooves 32 is distributed as evenly as possible over the circumference of the shoulders 28 and 31, so as to prevent relative cocking of the insert 21 and hub member 22 relative to each other; and b) The pins 30 engage the grooves 32 and settle into them only at one unique home position. At all other rotational positions, if any one pin 30 aligns with a given groove 32, the remaining pins 30 ride on the flat surface of the shoulder 31 and prevent the insert 21 and hub member 22 from engaging.

As shown schematically in FIG. 6, there are six pins 30 in the annular shoulder 28, disposed in three pairs. Each pair of pins is centered on a radius that is positioned 120 degrees from the centers of the other two pairs of pins 30. At each radius the respective pins of the associated pair are disposed at an angular separation $\theta_1$, $\theta_2$, and $\theta_3$ from the respective radius, so that each pair of pins has a different angular separation, for example, 5 degrees, 10 degrees and 15 degrees, respectively.

This arrangement fulfills the two criteria mentioned above, namely even axial displacement when the torque limit is exceeded, and no locking of the knob and shaft except at the home position.

The operation of the torque override feature can be explained with reference to FIGS. 7A to 7D.

In the home position shown in FIG. 7A, all the pins 30 are aligned with their respective grooves 32, and nest together as shown here. In this schematic, the pins are represented by a cylindrical protuberance, and in fact the protuberances could be molded or machined onto the flange 27 as unitary features.

As the associated knob rotates, the insert 21 moves (here to the right) and carries the hub member 22 with it until the torque limit is reached. Then, as shown in FIG. 7B, when the torque applied by insert 21 to the hub 22 exceeds the torque limit (which is programmed by the geometry of the pins 30 and grooves 32 and the characteristics of the spring 23), the cylindrical profiles of the pins 30 begin to ride up over the edges of the grooves 32. This pushes the knob 17 and insert 21 axially with respect to the hub member 22 and shaft 19. In this condition, also shown in FIG. 4, the pins 30 ride on the shoulder 31 and the spring is flexed so as to increase its axial force on the insert 21.

Upon further rotation of the knob 17, the pins 30 then slide along the flat surface of the shoulder 31 as shown in FIG. 7C. As rotation continues only relative angular displacement between the insert 21 and hub member 22 continues. At several intermediate positions between home position and the full-circle home position, one of the pins 30' will become aligned with one of the other grooves 32'. At these positions, as shown in FIG. 7D, the other pins 30 continue to ride on the flat surface of the shoulder 31. No two pins 30 coincide with any two grooves 32 except at the home position, at which all six coincide. Thus the pins 30 do not enter and engage in any grooves 32 except at the unique home position.

Figure 8:
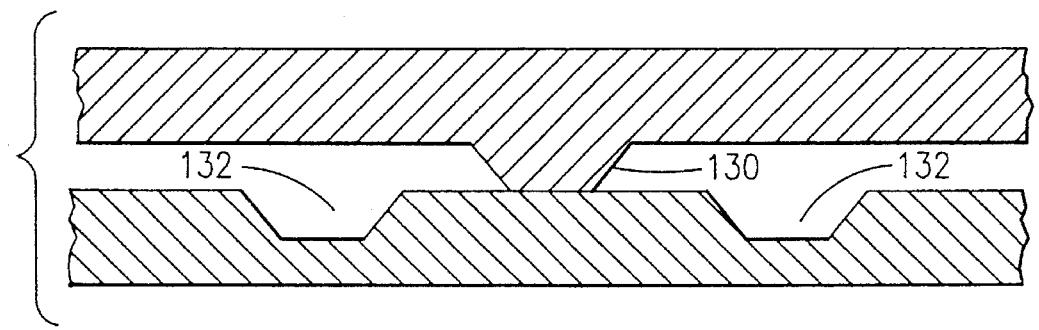
FIG. 8 is a schematic view illustrating an alternative embodiment.

FIG. 8 illustrates schematically one of many possible alternative arrangements. In this version rather than cylindrical protuberances or pins, there are a plurality of sprags 130 on the insert, each in the form of a prism of tetrahedral profile. The sprags have front and back sloping surface and a flat top surface. The corresponding grooves 132 have corresponding front and back ramp surfaces. The sprags 130 and grooves 132 are oriented radially with respect to their associated insert and hub members.

In other embodiments, the pins or similar structure can be disposed on the hub member, with the grooves situated on the insert. Also, a number of grooves and pins other than the six shown here can be used.

A variety of springs can be used, in addition to the disc spring shown here. For example, a disc spring with radial slits can be used. The slits permit the elastic force of the spring to be tailored to match a desired torque limit. Also, rather than a flat spring the disc spring can be dished in towards the insert, so as to produce an axial preload. This would minimize axial and radial backlash, and would permit the spring to have a somewhat reduced stiffness. Also, plural disc springs can be stacked together to achieve a desired spring force.

With the torque override feature 20 of this invention, there is a crisp snap or click when the knob 16 or 17 returns to its home position on its shaft 19. Even after the torque limit has been reached, steering is possible, in both directions at a torque somewhat less than that causing the insert 21 and the hub 22 to disengage. The torque override feature reengages by either turning back to the home position, or completing rotation, under slippage, until the full-circle home position is reached.

The knob assembly of this invention, with the torque override feature, can be retrofit onto an existing control handle in place of a standard knob assembly. Only the mechanism that includes the knob 16 or 17 with insert 21, the hub member 22, the spring 23, and the nut 24 need be changed. This retrofit can be carried out in the field, i.e., by the customer if necessary.

Of course, the torque override feature is not limited to applications with steerable probe devices such as that described here. In fact, this feature can be employed in a wide variety of applications where there is a hand-rotated knob drive, and where a torque limit must be observed.

While this invention has been described in detail with reference to selected preferred embodiments, the invention is not limited to those embodiments. Rather many modifications and variations will present themselves to persons skilled in this art without departure from the scope and spirit of this invention, as defined in the appended claims.

What is claimed is:

1. A hand-rotated knob drive for rotating a shaft-driven device comprising:

a hand-rotatable knob;

a drive stem on which said knob is mounted; and torque override means coupling said knob and said drive stem for:

(i) engaging the knob and the stem to enable said knob and stem to rotate as a unit until a predetermined torque is exceeded;

(ii) disengaging the knob from the stem to enable the knob to slip with respect to the stem after said predetermined torque has been exceeded; and (iii) re-engaging the knob to the stem after the knob and stem have been disengaged when a predetermined rotational alignment has been established therebetween.

2. A hand-rotated knob drive according to claim 1, wherein said torque override means includes an insert affixed in said knob and having an axial bore therethrough with a radial inward annular shoulder therein; a hub member mounted on said stem and having an annular recessed shoulder which mates with said inward annular shoulder with said hub member disposed within said bore; resilient means yieldably urging said hub member axially into said inward so that the insert annular shoulder and the hub member annular shoulder are urged into engagement with one another; a plurality of protuberances disposed at predetermined rotational positions on one of said shoulders; and a corresponding plurality of recesses disposed at positions on the other of said shoulders, such that said protuberances align and engage with said recesses at one and only one rotational position.

3. A hand-rotated knob drive according to claim 2, wherein said protuberances are disposed in three pairs, each pair being centered at a respective position 120 degrees from each of the other positions, and each pair of protuberances separated angularly from one another by a respective amount different from each of the other two pairs.

4. A hand-rotated knob drive according to claim 2, wherein said protuberances comprise generally cylindrical members having axes oriented radially on the respective shoulder, and the corresponding recesses are generally cylindrical grooves oriented radially in the other shoulder.

5. A hand-rotated knob drive according to claim 2, wherein said protuberances comprise generally trapezoidal prisms oriented radially on the respective shoulder.

6. A hand-rotated knob drive according to claim 2, wherein said resilient means comprises a flat spring having a rim pressing on said insert and a center attached to said hub member.

7. A hand-rotated knob drive according to claim 6, wherein said spring is a disc spring.

8. A control handle for a steerable probe or guide tube, comprising: a housing, shaft-driven means within the housing for effecting articulation of said probe or guide tube, and a hand-rotated knob drive for rotating said shaft-driven means, said knob drive including:

a hand-rotatable knob;

a drive stem on which said knob is mounted; and torque override means coupling said knob and said drive stem for:

(i) engaging the knob and stem to rotate as a unit until a predetermined torque is exceeded;

(ii) disengaging the knob from the stem to enable said knob to slip with respect to said stem after said predetermined torque has been exceeded; and (iii) re-engaging the knob to the stem after the knob and stem have been disengaged when a predetermined rotational alignment has been established therebetween.

9. A control handle according to claim 8, wherein said torque override means includes an insert affixed in said knob and having an axial bore therethrough with a radial inward annular shoulder therein; a hub member mounted on said stem and having annular recessed shoulder thereon which mates with said insert annular shoulder with said hub member disposed within said bore; resilient means yieldably urging said hub member axially into said insert so that the insert annular shoulder and the hub member annular shoulder are urged into engagement with one another; a plurality of protuberances disposed at predetermined rotational positions on one of said shoulders; and a corresponding plurality of recesses disposed at positions on the other of said shoulders, such that said protuberances align and engage with said recesses at one and only one rotational position.

10. A control handle according to claim 9, wherein said protuberances are disposed in three pairs, each pair being centered at a respective position 120 degrees from each of the other two positions; and each pair of protuberances being separated angularly from one another by a respective amount different from each of the other two pairs.

11. A control handle according to claim 8, wherein said knob has an index mark thereon to indicate the direction and amount of articulation of the probe when said torque override means is engaging the stem and the knob.

* * * * *

UNITED STATES PATENT AND TRADEMARK OFFICE
CERTIFICATE OF CORRECTION

PATENT NO. : 5,496,260
DATED : March 5, 1996
INVENTOR(S) : Allan I. Krauter, Michael P. Kehoskie and Robert L. Vivenzio It is certified that error appears in the above—identified patent and that said Letters Patent is hereby corrected as shown below:

Col. 3, line 30, change "B" to --3--
Col. 6, line 16, change "inward so that the insert annular shoulder" to --insert so that the inward annular shoulder--.

Signed and Sealed this

First Day of April, 1997

Attest:

BRUCE LEHMAN

Attesting Officer

Commissioner of Patents and Trademarks